United States Patent
MacDonald et al.

(10) Patent No.: US 6,240,919 B1
(45) Date of Patent: Jun. 5, 2001

(54) METHOD FOR PROVIDING RESPIRATORY AIRWAY SUPPORT PRESSURE

(76) Inventors: John J. MacDonald, 73890 Masson St., Palm Desert, CA (US) 92660; Ronald F. Richard, 31769 Poole Ct., Temecula, CA (US) 92591

(*) Notice: Subject to any disclaimer, the term of this patent is extended or adjusted under 35 U.S.C. 154(b) by 0 days.

(21) Appl. No.: 09/326,868

(22) Filed: Jun. 7, 1999

(51) Int. Cl.⁷ .................................................. A61M 16/00
(52) U.S. Cl. .............................. 128/204.18; 128/204.22
(58) Field of Search ........... 128/204.18, 204.21–204.24, 128/204.29, 205.18, 205.11, 205.24–205.26

(56) References Cited

U.S. PATENT DOCUMENTS

| | | | |
|---|---|---|---|
| Re. 29,778 | 9/1978 | Stewart | 128/145.8 |
| 1,406,141 | 2/1922 | Anston | 128/205.18 |
| 1,793,226 | 2/1931 | Eggleston et al. | |
| 2,503,563 | 4/1950 | Ray | 137/139 |
| 2,536,691 | 1/1951 | Miller et al. | 137/144 |
| 2,586,677 | 2/1952 | Marrett | 128/188 |
| 2,770,231 | 11/1956 | Falk | 128/29 |
| 2,770,232 | 11/1956 | Falk | 128/29 |
| 2,880,719 | 4/1959 | Andreasen | 128/29 |
| 2,892,348 | 6/1959 | Ekstrom, Jr. | 73/228 |
| 2,904,035 | 9/1959 | Andreasen | 128/29 |
| 3,007,490 | 11/1961 | Passmore | 137/599 |
| 3,015,963 | 1/1962 | Terry | 74/44 |
| 3,043,302 | 7/1962 | Spears et al. | 128/203 |
| 3,306,570 | 2/1967 | Cooksley | 251/30 |
| 3,351,057 | 11/1967 | Goodyear et al. | 128/188 |
| 3,374,410 | 3/1968 | Cronquist et al. | 318/138 |
| 3,386,458 | 6/1968 | Wasserman et al. | 137/114 |
| 3,403,556 | 10/1968 | Koester | 73/207 |

(List continued on next page.)

FOREIGN PATENT DOCUMENTS

| | | | |
|---|---|---|---|
| 2558935 | 7/1977 | (DE) | 73/861.53 |
| 3306607 | 9/1983 | (DE) | |
| 183396 | 6/1986 | (EP) | 604/283 |
| 2328452 | 10/1976 | (FR) | |
| 1541852 | 3/1979 | (GB) | |
| 2034387 | 2/1981 | (GB) | |

(List continued on next page.)

OTHER PUBLICATIONS

"Marks' Standard Handbook for Mechanical Engineers", 8th Edition, *Measurement of Fluid Flow Rate*, pp. 16–14 through 16–18 Westlake Plastics Co., "Thermalux Polysulfone", 1 page.

"Sandvik 11R51 Stainless Thin Strip", *Thin Strip with a Smooth Finish, Good Shape and High Fatigue Strength*, 4 pages.

"Microprocessor Control of Step Motors", Chapter 15, by S. H. Pollack, Step Motors and Control Systems, pp. 391–402, 1979.

*Primary Examiner*—Glenn K. Dawson
*Assistant Examiner*—Teena Mitchell
(74) *Attorney, Agent, or Firm*—Stetina Brunda Garred & Brucker

(57) ABSTRACT

A method of supporting respiratory airways during ventilator-assisted respiration. The method includes applying two supplemental pressure supports. The first such supplemental pressure support includes applying pressure of a first magnitude upon initiation of and for the duration of an inspiratory phase. The second supplemental pressure support includes applying pressure of a second magnitude greater than the first magnitude of the first supplemental pressure support upon initiation of and for the duration of the expiratory phase. In this manner, full time pressure augmentation is applied to respiratory airways to thereby structurally support the airways and thus maintain in an open configuration the pathways in communication with lungs.

4 Claims, 1 Drawing Sheet

U.S. PATENT DOCUMENTS

| | | | |
|---|---|---|---|
| 3,416,054 | 12/1968 | Galles | 318/138 |
| 3,450,382 | 6/1969 | Calim | 251/58 |
| 3,488,030 | 1/1970 | Hulme et al. | 251/134 |
| 3,509,895 | 5/1970 | Henneman | 137/81 |
| 3,569,813 | 3/1971 | Clark et al. | 318/569 |
| 3,579,279 | 5/1971 | Inaba et al. | 318/696 |
| 3,586,953 | 6/1971 | Markkamen et al. | 318/685 |
| 3,669,097 | 6/1972 | Fitz | 128/728 |
| 3,673,541 | 6/1972 | Volinskite | 439/195 |
| 3,675,633 | 7/1972 | Nakajima et al. | 123/119 A |
| 3,727,627 | 4/1973 | Bird et al. | 137/100 |
| 3,759,099 | 9/1973 | McGregor | 73/207 |
| 3,795,145 | 3/1974 | Miller | 73/213 |
| 3,813,592 | 5/1974 | Ryberg | 318/696 |
| 3,820,539 | 6/1974 | Ollivier | 128/145.8 |
| 3,839,662 | 10/1974 | Van | 318/160 |
| 3,840,006 | 10/1974 | Buck et al. | 128/145 |
| 3,842,389 | 10/1974 | Glover | 285/137.1 |
| 3,842,828 | 10/1974 | Bird | 128/145.8 |
| 3,896,837 | 7/1975 | Rohling | 137/110 |
| 3,904,174 | 9/1975 | Glese | 251/331 |
| 3,905,362 | 9/1975 | Eyrick et al. | 128/145.5 |
| 3,906,792 | 9/1975 | Miller | 73/213 |
| 3,910,112 | 10/1975 | Gerlach | 73/210 |
| 3,927,327 | 12/1975 | Bermas | 250/470 |
| 3,961,627 | 6/1976 | Ernst et al. | 128/145.8 |
| 3,964,310 | 6/1976 | Stenberg | 73/207 |
| 3,968,416 | 7/1976 | Leenhouts | 318/696 |
| 3,972,327 | 8/1976 | Ernst et al. | 128/145.8 |
| 3,985,124 | 10/1976 | Coleman | 128/727 |
| 3,985,131 | 10/1976 | Buck et al. | 128/145.8 |
| 4,006,634 | 2/1977 | Billette et al. | 73/207 |
| 4,024,447 | 5/1977 | Epstein | 318/696 |
| 4,027,636 | 6/1977 | Yamamoto et al. | 123/119 A |
| 4,031,448 | 6/1977 | Adachi | 318/696 |
| 4,036,221 | 7/1977 | Hillsman et al. | 128/145.6 |
| 4,076,279 | 2/1978 | Klotz et al. | 285/137.1 |
| 4,081,736 | 3/1978 | Leenhouts et al. | 318/696 |
| 4,083,245 | 4/1978 | Osborn | 73/207 |
| 4,087,732 | 5/1978 | Pritchard | 318/696 |
| 4,094,285 | 6/1978 | Oyama et al. | 123/119 A |
| 4,107,594 | 8/1978 | Jacobs | 318/685 |
| 4,112,757 | 9/1978 | Hayward | 73/207 |
| 4,114,601 | 9/1978 | Abels | 128/1 R |
| 4,119,902 | 10/1978 | Newell | 318/696 |
| 4,121,578 | 10/1978 | Torzala | 128/142 R |
| 4,126,818 | 11/1978 | Taylor | 318/46 |
| 4,126,821 | 11/1978 | Cannon | 318/696 |
| 4,153,021 | 5/1979 | Hattori et al. | 123/119 EC |
| 4,158,351 | 6/1979 | Ando et al. | 123/119 A |
| 4,171,697 | 10/1979 | Arion | 128/145.8 |
| 4,176,687 | 12/1979 | Ensign | 137/625.65 |
| 4,177,830 | 12/1979 | Munson | 137/501 |
| 4,181,108 | 1/1980 | Bellicardi | 123/119 EC |
| 4,193,301 | 3/1980 | Ferrentino | 73/207 |
| 4,199,132 | 4/1980 | deMey, II | 251/134 |
| 4,204,536 | 5/1980 | Albarda | 128/204.22 |
| 4,214,593 | 7/1980 | Imbruce et al. | 128/748 |
| 4,235,105 | 11/1980 | Walters | 73/861.53 |
| 4,256,100 | 3/1981 | Levy et al. | 128/204.21 |
| 4,256,101 | 3/1981 | Ellestad | 128/204.23 |
| 4,266,573 | 5/1981 | Braatz | 137/630.18 |
| 4,281,651 | 8/1981 | Cox | 128/204.23 |
| 4,285,496 | 8/1981 | Coles | 251/130 |
| 4,297,998 | 11/1981 | Christianson | 128/204.26 |
| 4,301,810 | 11/1981 | Belman | 128/200.24 |
| 4,304,136 | 12/1981 | McCabe et al. | 73/861.54 |
| 4,323,064 | 4/1982 | Hoenig et al. | 128/204.21 |
| 4,326,513 | 4/1982 | Schulz et al. | 128/283.14 |
| 4,327,720 | 5/1982 | Bronson et al. | 128/207.15 |
| 4,328,823 | 5/1982 | Schreiber | 137/88 |
| 4,333,453 | 6/1982 | Rodder | 128/205.24 |
| 4,334,534 | 6/1982 | Ozaki | 128/207.15 |
| 4,336,590 | 6/1982 | Jacq et al. | 364/418 |
| 4,350,050 | 9/1982 | Nelson | 73/861.54 |
| 4,368,646 | 1/1983 | Roqq | 73/861.55 |
| 4,393,869 | 7/1983 | Boyarsky et al. | 128/204.18 |
| 4,401,116 | 8/1983 | Fry et al. | 128/205.24 |
| 4,421,113 | 12/1983 | Gedeon et al. | 128/204.23 |
| 4,433,685 | 2/1984 | Giorgini et al. | 128/204.26 |
| 4,436,090 | 3/1984 | Darling | 128/204.26 |
| 4,448,192 | 5/1984 | Stawitcke et al. | 128/204.26 |
| 4,457,304 | 7/1984 | Molnar et al. | 128/204.25 |
| 4,457,339 | 7/1984 | Juan et al. | 137/624.16 |
| 4,459,982 | 7/1984 | Fry | 128/204.23 |
| 4,462,410 | 7/1984 | Blais et al. | 128/727 |
| 4,474,068 | 10/1984 | Knetsch et al. | 73/861.53 |
| 4,484,554 | 11/1984 | Nakajima et al. | 123/339 |
| 4,487,207 | 12/1984 | Fitz | 128/728 |
| 4,493,614 | 1/1985 | Chu et al. | 417/22 |
| 4,524,804 | 6/1985 | Goedecke et al. | 137/625.64 |
| 4,526,431 | 7/1985 | Kasukawa | 439/353 |
| 4,527,557 | 7/1985 | DeVries et al. | 128/204.23 |
| 4,535,816 | 8/1985 | Feder et al. | 137/625.65 |
| 4,540,018 | 9/1985 | Dantlgraber | 137/540 |
| 4,548,382 | 10/1985 | Otting | 251/5 |
| 4,552,027 | 11/1985 | Larner | 73/861.53 |
| 4,561,408 | 12/1985 | Jenkins | 123/571 |
| 4,570,631 | 2/1986 | Durkan | 128/204.23 |
| 4,576,159 | 3/1986 | Hahn et al. | 128/203.14 |
| 4,579,145 | 4/1986 | Leiber et al. | 137/625.65 |
| 4,587,967 | 5/1986 | Chu et al. | 128/204.21 |
| 4,592,349 | 6/1986 | Bird | 128/204.25 |
| 4,597,387 | 7/1986 | Carnegie et al. | 128/201.27 |
| 4,602,653 | 7/1986 | Ruiz-Vela et al. | 137/88 |
| 4,604,902 | 8/1986 | Sabin et al. | 73/861.04 |
| 4,606,340 | 8/1986 | Ansite | 128/205.24 |
| 4,611,591 | 9/1986 | Inui et al. | 128/205.24 |
| 4,614,122 | 9/1986 | Graves | 73/861.74 |
| 4,617,637 | 10/1986 | Chu et al. | 364/505 |
| 4,619,139 | 10/1986 | Rosaen | 73/198 |
| 4,635,631 | 1/1987 | Izumi | 128/204.23 |
| 4,677,603 | 6/1987 | Kenjyo | 369/32 |
| 4,686,974 | 8/1987 | Sato et al. | 128/204.23 |
| 4,688,433 | 8/1987 | Silverwater | 73/861.53 |
| 4,699,137 | 10/1987 | Schroeder | 128/205.24 |
| 4,701,159 | 10/1987 | Brown et al. | 285/137.1 |
| 4,702,240 | 10/1987 | Chaoui | 128/204.18 |
| 4,723,948 | 2/1988 | Clark et al. | 604/283 |
| 4,726,366 | 2/1988 | Apple | 128/205.18 |
| 4,776,333 | 10/1988 | Miyamae | 128/204.21 |
| 4,790,194 | 12/1988 | Bellows et al. | 73/861.53 |
| 4,821,715 | 4/1989 | Downing | 128/207.18 |
| 4,821,767 | 4/1989 | Jackson | 137/491 |
| 4,823,788 | 4/1989 | Smith et al. | 128/204.21 |
| 4,838,257 | 6/1989 | Hatch | 128/204.18 |
| 4,840,457 | 6/1989 | Remer | 350/255 |
| 4,854,574 | 8/1989 | Larson et al. | 272/99 |
| 4,895,570 | 1/1990 | Larkin | 604/905 |
| 4,898,174 | 2/1990 | Fangrow, Jr. | 128/204.24 |
| 4,900,065 | 2/1990 | Houck | 285/137.1 |
| 4,957,107 | 9/1990 | Sipin | 128/204.21 |
| 4,966,193 | 10/1990 | De Campos | 137/625.35 |
| 4,971,049 | 11/1990 | Rotariu et al. | 128/204.21 |
| 4,993,269 | 2/1991 | Guillaume et al. | 73/861.53 |
| 5,014,694 | 5/1991 | DeVries | 128/205.24 |
| 5,044,362 | 9/1991 | Younes | 128/204.21 |
| 5,047,021 | 9/1991 | Utterberg | 604/238 |
| 5,052,386 | 10/1991 | Fischer, Jr. | 285/322 |
| 5,072,729 | 12/1991 | DeVries | 128/204.23 |
| 5,099,635 | 3/1992 | Butkovich et al. | 56/13.5 |

| | | | |
|---|---|---|---|
| 5,101,820 | * 4/1992 | Christopher | 128/204.18 |
| 5,103,814 | * 4/1992 | Maher | 128/204.18 |
| 5,107,830 | 4/1992 | Younes | 128/204.18 |
| 5,117,819 | * 6/1992 | Servidio et al. | 128/204.18 |
| 5,127,400 | 7/1992 | DeVries et al. | 128/205.24 |
| 5,137,524 | 8/1992 | Lynn et al. | 604/283 |
| 5,148,802 | * 9/1992 | Sanders et al. | 128/204.23 |
| 5,159,924 | 11/1992 | Cegielski et al. | 128/203.12 |
| 5,161,525 | 11/1992 | Kimm et al. | 128/204.26 |
| 5,197,895 | 3/1993 | Stupecky | 439/194 |
| 5,199,424 | * 4/1993 | Sullivan et al. | 128/204.18 |
| 5,239,995 | 8/1993 | Estes et al. | 128/204.23 |
| 5,313,937 | * 5/1994 | Zdrojkowski | 128/204.23 |
| 5,315,990 | * 5/1994 | Mondry | 128/205.11 |
| 5,405,269 | 4/1995 | Stupecky | 439/191 |
| 5,433,193 | * 7/1995 | Sanders et al. | 128/204.23 |
| 5,452,714 | * 9/1995 | Anderson et al. | 128/205.11 |
| 5,537,997 | * 7/1996 | Mechlenburg et al. | 128/204.23 |
| 5,540,219 | * 7/1996 | Mechlenburg et al. | 128/204.23 |
| 5,868,133 | 2/1999 | DeVries et al. | 128/204.21 |
| 6,000,396 | * 12/1999 | Melker et al. | 128/204.21 |
| 6,076,523 | * 6/2000 | Jones et al. | 128/205.11 |
| 6,123,074 | * 9/2000 | Hete et al. | 128/204.21 |

FOREIGN PATENT DOCUMENTS

| | | | |
|---|---|---|---|
| 2121292 | 12/1983 | (GB) . | |
| 2126666 | 3/1984 | (GB) | F04B/21/02 |
| 2166360A | 5/1986 | (GB) | A61M/16/01 |
| PCT/US82/ 00795 | 6/1982 | (WO) | A61B/5/08 |
| PCT/FR93/ 00547 | 12/1993 | (WO) . | |

OTHER PUBLICATIONS

"Electric Motors & control Techniques", by Irving M. Gottlieb, Stepper Motor Controller, pp. 183–198 and index, 1982.

"Step Motors and Control Systems", Edited by Benjamin C. Kuo, "Drive Circuitry For Step Motors", pp. 114–143 and index, Chapter 4, 1979.

"Stepping Motors and Their Microprocessor Controls" by Takashi Kenjo, "Drive System and Circuitry For Open–Loop Control of Stepping Motors", pp. 121–165 (Chapter 5) 1984.

"Servo Ventilator 900B—Service Manual", by Siemens–Elema, 55 pages plus front and back matter, 1979.

Computer printouts containing abstracts of 62 pages.

* cited by examiner

METHOD FOR PROVIDING RESPIRATORY AIRWAY SUPPORT PRESSURE

CROSS-REFERENCE TO RELATED APPLICATIONS (Not Applicable)

STATEMENT RE: FEDERALLY SPONSORED RESEARCH/DEVELOPMENT (Not Applicable)

BACKGROUND OF THE INVENTION

The present invention relates in general to respiratory ventilation, and in particular to methodology for providing pressure support to respiratory airways during ventilator-assisted respiration.

Certain respiratory diseases not only require patient special care with respect to physical activity and attendant exertion levels, but also require specialized mechanical augmentation to permit the patient to maintain pressure support to respiratory airways. Thus, while lung dysfunction, lung tissue degradation, autonomic nervous system disability, etc. can deprive an individual of adequate oxygenation and attendant carbon dioxide removal, dysfunctional air delivery conduits also can contribute to reduced respiratory efficiency since affected respiratory airways may lack adequate support to maintain adequate structural stability during the respiration process.

One present method for treating airway malfunction provides for positive end expiratory pressure application by a ventilator. A second treatment method is a widely-used breathing technique called "pursed lip breathing." Both procedures involve back pressure applied to the respiratory airways to thereby attempt to maintain airway structure and resultant passageway openness. While these approaches certainly aid respiration, it is generally recognized that their respective adequacies can be improved. Accordingly, a primary object of the present invention is to provide a method of supporting respiratory airways by applying variable pressure magnitudes depending upon the timing within the respiratory cycle.

Another object of the present invention is to provide methodology for supporting respiratory airways in association with delivery thereof by a ventilator.

Yet another object of the present invention is to provide respiratory airway support wherein traditional positive end expiratory pressure is augmented with supplemental pressure support.

These and other objects of the present invention will become apparent throughout the description thereof which now follows.

BRIEF SUMMARY OF THE INVENTION

The present invention is a method of supporting respiratory airways during ventilator-assisted respiration where the ventilator maintains a positive end expiratory pressure in the respiratory airways during the expiratory phase. The method comprises first activating the ventilator to maintain the positive end expiratory pressure, and thereafter applying two supplemental pressure supports. The first such supplemental pressure support comprises applying pressure of a magnitude greater than the positive end expiratory pressure and occurs upon initiation of and for the duration of an inspiratory phase. The second supplemental pressure support comprises applying pressure of a magnitude greater than the first supplemental pressure support and occurs upon initiation of and for the duration of the patent expiratory flow. In this manner, proper lung evacuation can occur throughout each expiratory cycle by supporting respiratory airways throughout the respiration cycle. Thus, the pressure of inspiratory air, already positive-pressure-influenced by inhalation, is amplified through the addition of the first supplemental pressure upon initiation of and for the duration of inhalation to thereby provide a slight inspiratory boost for offsetting anatomical positive end expiratory pressure. Continued respiratory airway support occurs during the expiration cycle by introducing the second supplemental pressure upon initiation of and throughout exhalation to thereby increase already-present positive end expiratory pressure and intensify respiratory airway support. Consequently, full time pressure augmentation is applied to respiratory airways to thereby structurally support the airways and thus maintain in an open configuration the pathways in communication with lungs.

BRIEF DESCRIPTION OF THE SEVERAL VIEWS OF THE DRAWING

An illustrative and presently preferred embodiment of the invention is shown in the accompanying drawings in which.

DETAILED DESCRIPTION OF THE INVENTION

Figure 1:
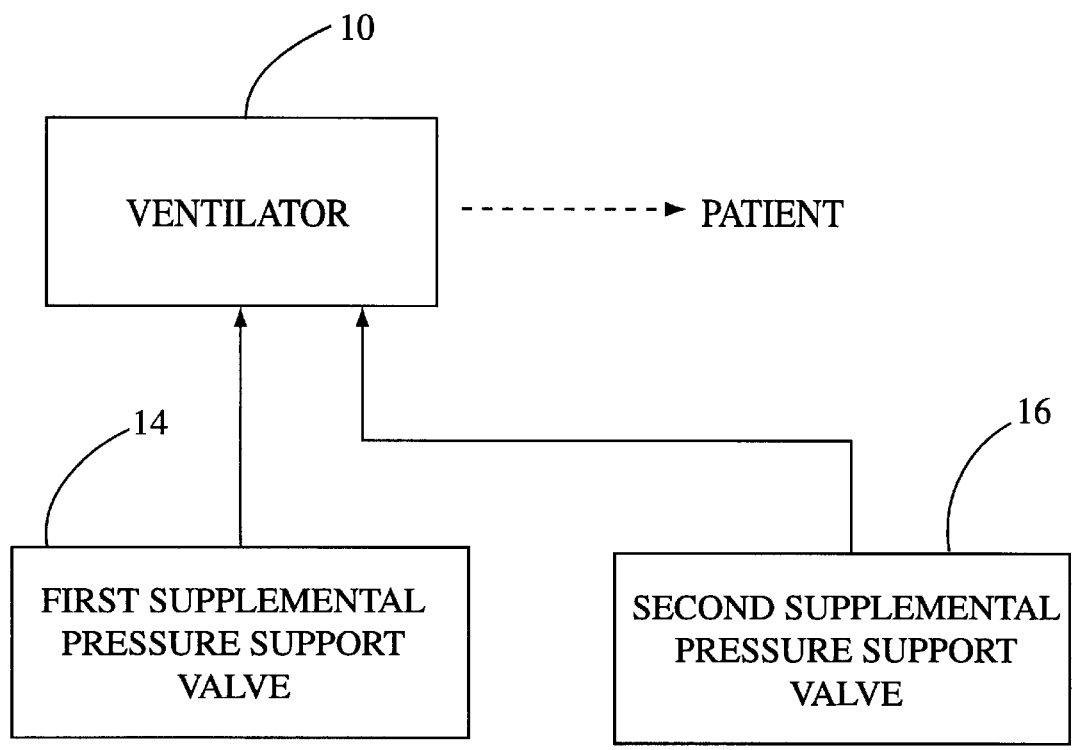
FIG. 1 is a flow chart defining operation of a ventilator in the provision of support to respiratory airways during ventilator-assisted respiration.

Referring to the drawing figure, a respiratory ventilator 10 is provided for maintaining a positive end expiratory pressure in the respiratory airways of a patient being treated. The ventilator 10 is equipped to conventionally provide selectable supplemental air pressure during both inhalation and exhalation through, respectively, first 14 and second 16 supplemental pressure support valves. An operator first connects the ventilator 10 to a patient, and thereafter adjusts the second supplemental pressure support valve 16 to produce a desired positive expiratory pressure to be applied to respiratory airways during exhalation. Once this positive expiratory pressure is chosen, the operator then provides supplemental pressure to the respiratory airways of the patient by activating the first supplemental pressure support valve 14 to deliver pressure upon initiation of and for the duration of each inspiratory phase of respiration. Non-limiting exemplification of one treatment regimen provides a selected first supplemental pressure magnitude from about four to about seven $cmH_2O$. Concurrent with initiation of delivery of first supplemental pressure is activation of the second supplemental pressure support valve 16 to thereby apply second supplemental pressure of a magnitude greater than the first supplemental pressure and delivered upon initiation of and for the duration of the expiratory phase. Continued non-limiting exemplification of the preceding treatment regimen provides a selected second supplemental pressure magnitude should be from about six to about 12 $cmH_2O$.

As earlier related, supplemental support of respiratory airways throughout the respiration cycle contributes toward proper lung evacuation in patients experiencing airway malfunctions. Thus, the pressure of inspiratory air, already under pressure through normal inhalation action, is amplified through the addition of the first supplemental pressure upon initiation of inhalation and throughout its course to thus provide an inspiratory assist in equalizing anatomical positive end expiratory pressure. Continued respiratory airway support occurs during expiration by introducing the second supplemental pressure upon initiation of exhalation and throughout its duration to thereby continue intensification of respiratory airway support. In this manner, full time pressure augmentation is applied to respiratory airways during both inhalation and exhalation to thereby structurally support the airways in an open configuration for air ingression and egression.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

What is claimed is:

1. A method of supporting respiratory airways during ventilator-assisted respiration, the method comprising:

a) applying a first supplemental pressure support comprising pressure of a first magnitude in said respiratory airways upon initiation of and for the duration of an inspiratory phase; and b) applying a second supplemental pressure support comprising pressure of a second magnitude greater than said first magnitude of said first supplemental pressure support in said respiratory airways upon initiation of and for the duration of said expiratory phase.

2. A method of supporting respiratory airways as claimed in claim 1 wherein the first magnitude of the said first supplemental pressure support is from about four to about seven cmH$_2$O.

3. A method of supporting respiratory airways as claimed in claim 2 wherein the second magnitude of said second supplemental pressure support is from about six to about 12 cmH$_2$O.

4. A method of supporting respiratory airways as claimed in claim 1 comprising in addition monitoring the ventilator for leakage of said first supplemental pressure support, and second supplemental pressure support.

* * * * *